(12) United States Patent
Shin et al.

(10) Patent No.: US 11,673,487 B2
(45) Date of Patent: Jun. 13, 2023

(54) PASSENGER IDENTIFICATION APPARATUS FOR VEHICLES

(71) Applicants: Hyundai Motor Company, Seoul (KR); Kia Motors Corporation, Seoul (KR)

(72) Inventors: Pyoung Sik Shin, Gyeonggi-do (KR); Chun Seok Park, Incheon (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 897 days.

(21) Appl. No.: 16/592,369

(22) Filed: Oct. 3, 2019

(65) Prior Publication Data
US 2020/0361342 A1 Nov. 19, 2020

(30) Foreign Application Priority Data
May 13, 2019 (KR) .................. 10-2019-0055685

(51) Int. Cl.
*B60N 2/00* (2006.01)
*B60N 2/42* (2006.01)
*B60N 2/56* (2006.01)

(52) U.S. Cl.
CPC .............. *B60N 2/002* (2013.01); *B60N 2/42* (2013.01); *B60N 2/5678* (2013.01)

(58) Field of Classification Search
CPC ........ B60N 2/002; B60N 2/42; B60N 2/5678; B60R 21/01542; B60R 21/01544
See application file for complete search history.

(56) References Cited

U.S. PATENT DOCUMENTS

| | | | | |
|---|---|---|---|---|
| 7,614,314 B2 * | 11/2009 | Park | ................. | B60R 21/01532 73/862.626 |
| 7,928,341 B2 * | 4/2011 | Ito | ........................ | B60N 2/5685 219/202 |
| 9,428,080 B2 * | 8/2016 | Kordel | ................. | B60N 2/7094 |
| 2015/0123436 A1 * | 5/2015 | Boyer | .................... | G01G 19/08 297/217.2 |
| 2019/0092204 A1 * | 3/2019 | Mergl | .................... | A61H 23/02 |

FOREIGN PATENT DOCUMENTS

| | | | |
|---|---|---|---|
| JP | 6031395 B2 | | 11/2016 |
| KR | 10-2010-0045781 A | | 5/2010 |
| KR | 100999681 B1 | * | 12/2010 |
| KR | 10-1406431 B1 | | 6/2014 |
| KR | 101406431 B1 | * | 6/2014 |

* cited by examiner

*Primary Examiner* — Milton Nelson, Jr.
(74) *Attorney, Agent, or Firm* — Fox Rothschild LLP

(57) ABSTRACT

A passenger identification apparatus for vehicles is provided to identify a passenger through integration of a sensor that senses change in permittivity and a sensor that senses change in pressure. The apparatus includes a permittivity change sensing unit that is installed in the seat and senses change in capacitance generated by permittivity of the passenger seated on the seat and a pressure change sensing unit that is installed in the seat and senses change in pressure generated by a load of the passenger seated on the seat. A controller adjusts power supplied to the permittivity change sensing unit and the pressure change sensing unit and determines whether the passenger is seated on the seat and the type of passenger using permittivity and pressure change values sensed by the permittivity change sensing unit and the pressure change sensing unit.

10 Claims, 4 Drawing Sheets

PASSENGER IDENTIFICATION APPARATUS FOR VEHICLES

CROSS-REFERENCE TO RELATED APPLICATION

This application claims the priority benefit of Korean Patent Application No. 10-2019-0055685, filed on May 13, 2019, the disclosure of which is incorporated herein by reference.

BACKGROUND

1. Field of the Invention

The present invention relates to a passenger identification apparatus for vehicles, and more particularly to a passenger identification apparatus for vehicles which identifies a passenger through integration of a sensor that senses change in permittivity and a sensor that senses change in pressure.

2. Description of the Related Art

In general, various safety apparatuses for ensuring passenger safety are provided in a vehicle, and an airbag which inflates between a vehicle structure and a passenger to protect the passenger during a vehicle collision, corresponds to one of such safety apparatuses. Such an airbag is deployed to protect the passenger in a vehicle collision. However, the inflating airbag may be dangerous for a child due to the location of the airbag relative to the child. Therefore, to determine deployment of the airbag, it is important to determine whether a passenger is seated on each seat and whether the passenger is an adult, a child of 6 years old or younger, or an infant of 1 year old or younger.

Technologies to identify a passenger seated on a seat may be generally divided into a method using a seat belt reminder (SBR) and a method using an occupant detection sensor (ODS). The SBR method functions to inform a passenger of whether the passenger wears a seat belt after the passenger is seated on a seat through a warning sound or a warning light, and uses technology which detects whether a passenger is seated on a seat by sensing change in pressure applied according to the load of the passenger, as passenger identification technology.

The SBR method is advantageous in that whether a passenger is seated on a seat may be sensed, but an error in identification of the passenger may frequently occur due to a substantial difference in the load of the passenger sensed according to the posture of the passenger seated on the seat. Further, even when a passenger is not seated on the seat but an article having a load is placed on the seat, this may be erroneously sensed as a passenger on the seat.

Further, the occupant detection sensor (ODS) method uses technology which detects whether a passenger is seated on a seat by sensing change in permittivity according to an article placed on the seat. The occupant detection sensor (ODS) method is advantageous in that whether there is an article placed on a seat may be sensed, but, even if a passenger is not seated on the seat but an article having a small load, such as electronic equipment, is placed on the seat, it may be erroneously sensed as a passenger on the seat.

The above description has been provided to aid in understanding of the background of the present invention and should not be interpreted as conventional technology known to those skilled in the art.

SUMMARY

Therefore, the present invention provides a passenger identification apparatus for vehicles which may reduce errors in passenger identification both using a sensor configured to sense change in permittivity and a sensor configured to sense change in pressure.

In accordance with the present invention, the above and other objects may be accomplished by the provision of a passenger identification apparatus for vehicles which identifies a passenger seated on a seat for vehicles and may include a permittivity change sensing unit installed in the seat, and configured to sense change in capacitance generated by permittivity of the passenger seated on the seat, a pressure change sensing unit installed in the seat, and configured to sense change in pressure generated by a load of the passenger seated on the seat, and a controller configured to adjust power supplied to the permittivity change sensing unit and the pressure change sensing unit and to determine whether the passenger is seated on the seat and the type of the passenger using permittivity and pressure change values sensed by the permittivity change sensing unit and the pressure change sensing unit.

The permittivity change sensing unit and the pressure change sensing unit may be separately installed in different areas of the seat, and be electrically connected in parallel. The controller may include a switch configured to switch between the permittivity change sensing unit and the pressure change sensing unit to selectively supply power to the permittivity change sensing unit and the pressure change sensing unit.

Additionally, the permittivity change sensing unit may include a first permittivity electrode configured to sense change in permittivity of the passenger seated on the seat, a second permittivity electrode spaced apart downward from the first permittivity electrode to be opposite thereto, and configured to prevent an ambient noise signal from being sensed by the first permittivity electrode, and a first insulator interposed between the first permittivity electrode and the second permittivity electrode to insulate the first permittivity electrode and the second permittivity electrode from each other. The pressure change sensing unit may be disposed to be spaced apart from the permittivity change sensing unit in the horizontal direction and may include a first pressure electrode and a second pressure electrode spaced apart from each other in the vertical direction to be opposite to each other. A spacer may be interposed between the first pressure electrode and the second pressure electrode to maintain a distance between the first pressure electrode and the second pressure electrode in response to change in the distance between the first pressure electrode and the second pressure electrode. Additionally, a second insulator and a third insulator may be disposed on outer surfaces of the first pressure electrode and the second pressure electrode to insulate the first pressure electrode and the second pressure electrode.

The permittivity change sensing unit and the pressure change sensing unit may be installed in the same area of the seat to be disposed in the vertical direction, and be electrically connected in parallel. The controller may include a switch configured to switch between the permittivity change sensing unit and the pressure change sensing unit to selectively supply power to the permittivity change sensing unit and the pressure change sensing unit.

Additionally, the permittivity change sensing unit may include a first permittivity electrode configured to sense change in permittivity of the passenger seated on the seat, a second permittivity electrode spaced apart downward from the first permittivity electrode to be opposite thereto, and configured to prevent an ambient noise signal from being sensed by the first permittivity electrode, and a first insulator interposed between the first permittivity electrode and the second permittivity electrode to insulate the first permittivity electrode and the second permittivity electrode from each other. The pressure change sensing unit may be disposed under the permittivity change sensing unit and may include a first pressure electrode and a second pressure electrode spaced apart from each other in the vertical direction to be opposite to each other. A spacer may be interposed between the first pressure electrode and the second pressure electrode to maintain a distance between the first pressure electrode and the second pressure electrode in response to change in the distance between the first pressure electrode and the second pressure electrode. Additionally, a second insulator and a third insulator may be disposed on outer surfaces of the first pressure electrode and the second pressure electrode to insulate the first pressure electrode and the second pressure electrode. The second insulating of the press change sensing unit may be disposed to contact a lower surface of the second permittivity electrode of the permittivity change sensing unit.

The permittivity change sensing unit may include a first permittivity electrode configured to sense change in permittivity of the passenger seated on the seat, and a first insulator disposed under the first permittivity electrode. The pressure change sensing unit may be disposed under the permittivity change sensing unit and may include a first pressure electrode and a second pressure electrode spaced apart from each other in the vertical direction to be opposite to each other. A spacer may be interposed between the first pressure electrode and the second pressure electrode to maintain a distance between the first pressure electrode and the second pressure electrode in response to change in the distance between the first pressure electrode and the second pressure electrode. A second insulator and a third insulator may be interposed between the first pressure electrode and the spacer and between the spacer and the second pressure electrode to insulate the first pressure electrode, the spacer and the second pressure electrode from one another. The first pressure electrode of the pressure change sensing unit may be disposed to contact a lower surface of the first insulator of the permittivity change sensing unit.

Further, the permittivity change sensing unit and the pressure change sensing unit may be separately installed in different areas of the seat or be installed in the same area of the seat to be disposed in the vertical direction, and be electrically connected in series, and the controller may be configured to alternately supply alternating current (AC) power provided to the permittivity change sensing unit and direct current (DC) power provided to the pressure change sensing unit.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Reference will now be made in detail to the exemplary embodiments of the present invention, examples of which are illustrated in the accompanying drawings. Wherever possible, the same reference numbers will be used throughout the drawings to refer to the same or like parts.

Figure 1:
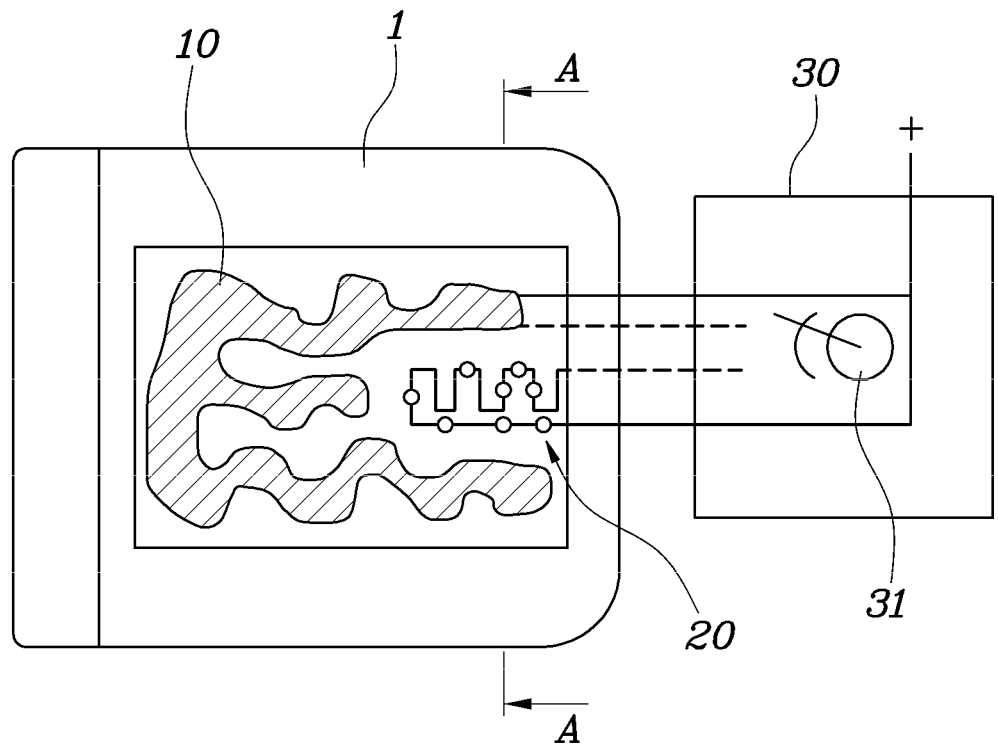
FIG. 1 is a view illustrating the configuration of a passenger identification apparatus for vehicles in accordance with a first exemplary embodiment of the present invention.
Figure 2:
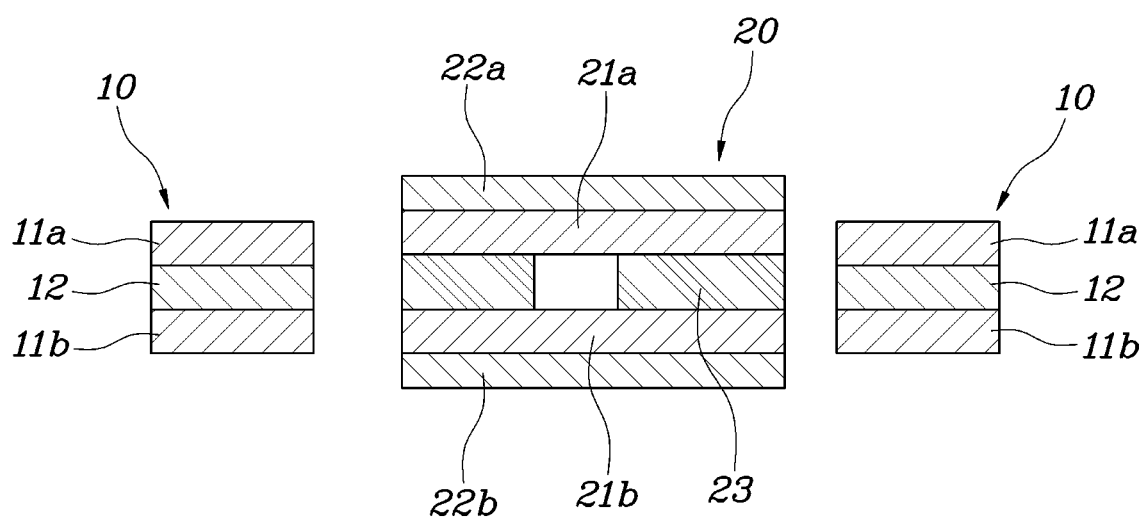
FIG. 2 is a view illustrating the configurations of a permittivity change sensing unit and a pressure change sensing unit in accordance with the first exemplary embodiment of the present invention.

FIG. 1 is a view illustrating the configuration of a passenger identification apparatus for vehicles in accordance with a first exemplary embodiment of the present invention, and FIG. 2 is a view illustrating the configurations of a permittivity change sensing unit and a pressure change sensing unit in accordance with the first exemplary embodiment of the present invention.

As exemplarily shown in FIGS. 1 and 2, the passenger identification apparatus for vehicles in accordance with the first exemplary embodiment of the present invention may be configured to identify whether a passenger is seated on a seat 1 provided in a vehicle and a type of passenger, and may include a permittivity change sensing unit 10 installed in the seat 1 to sense change in capacitance generated by permittivity of the passenger seated on the seat 1, a pressure change sensing unit 20 installed in the seat 1 to sense change in pressure generated by a load of the passenger seated on the seat 1, and a controller 30 configured to adjust power supplied to the permittivity change sensing unit 10 and the pressure change sensing unit 20 and determine whether the passenger is seated on the seat 1 and the type of passenger using permittivity and pressure change values sensed by the permittivity change sensing unit 10 and the pressure change sensing unit 20.

Particularly, the permittivity change sensing unit 10 and the pressure change sensing unit 20 may be installed separately in different areas of the seat 1, and may be electrically connected in parallel. Therefore, the controller 30 may include a switch 31 to switch between the permittivity change sensing unit 10 and the pressure change sensing unit 20 to selectively supply power to the permittivity change sensing unit 10 and the pressure change sensing unit 20. The permittivity change sensing unit 10 may be configured to identify whether the passenger is seated on the seat 1 by sensing change in capacitance generated by permittivity of the passenger seated on the seat 1.

As exemplarily shown in FIG. 2, the permittivity change sensing unit 10 may include a first permittivity electrode 11a configured to sense change in permittivity of the passenger seated on the seat 1, a second permittivity electrode 11b spaced apart downward from the first permittivity electrode 11a to be opposite from the first permittivity electrode 11a and configured to prevent an ambient noise signal from being sensed by the first permittivity electrode 11a, and a first insulator 12 interposed between the first permittivity electrode 11a and the second permittivity electrode 11b to insulate the first permittivity electrode 11a and the second permittivity electrode 11b from each other.

The first permittivity electrode 11a and the second permittivity electrode 11b may identify whether the passenger is seated on the seat 1 and a type of passenger by sensing permittivity of the passenger seated on the seat 1 or an article placed on the seat 1. The first permittivity electrode 11a and the second permittivity electrode 11b may be configured to identify whether the passenger is seated on the seat 1 and a kind of the passenger by detecting change in capacitance generated by change in permittivity. The permittivity change sensing unit 10 uses a principle that capacitance is directly proportional to change in permittivity.

Particularly, the first permittivity electrode 11a may be configured to determine whether the passenger is seated on the seat 1 and a type of passenger by sensing a permittivity difference of the passenger or the article on the seat 1. The sensing of the permittivity difference indicates that the permittivity difference causes a current difference and the current difference is sensed by the controller 30.

Further, the pressure change sensing unit 20 may be configured to determine whether the passenger is seated on the seat 1 by sensing change in an amount of the seat 1 pressurized by a load of the passenger seated on the seat 1. In particular, the pressure change sensing unit 20 uses a principle that capacitance is inversely proportional to a distance between electrodes. The sensing of change in the amount of the pressurized seat 1 indicates that a difference in pressurizing force causes a difference in the distance between the electrodes, the distance difference causes a current difference, and the current difference may be sensed by the controller 30. The pressure change sensing unit 20 may be disposed in a different area from the position of the permittivity change sensing unit 10 within the seat 1 to be spaced apart from the permittivity change sensing unit 10 in the horizontal direction.

As exemplarily shown in FIG. 2, the pressure change sensing unit 20 may include a first pressure electrode 21a and a second pressure electrode 21b spaced apart from each other in the vertical direction to be opposite to each other, a spacer 23 interposed between the first pressure electrode 21a and the second pressure electrode 21b to maintain a distance between the first pressure electrode 21a and the second pressure electrode 21b in response to change in the distance between the first pressure electrode 21a and the second pressure electrode 21b, and a second insulator 22a and a third insulator 22b disposed on the outer surfaces of the first pressure electrode 21a and the second pressure electrode 21b to insulate the first pressure electrode 21a and the second pressure electrode 21b.

In particular, the first pressure electrode 21a and the second pressure electrode 21b may be configured to determine whether the passenger is seated on the seat 1 and a type of passenger by sensing change in the distance between the first pressure electrode 21a and the second pressure electrode 21b by pressurizing force according to the load of the passenger seated on the seat 1 or the article placed on the seat 1. In the above-described passenger identification apparatus for vehicles in accordance with the first exemplary embodiment, if a passenger is seated on the seat 1, the controller 30 may be configured to alternately supply power to the permittivity change sensing unit 10 and the pressure change sensing unit 20.

Then, permittivity detected by the first permittivity electrode 11a is changed by the passenger, and the controller 30 may be configured to determine whether the passenger is seated on the seat 1 and a type of passenger by sensing such change in permittivity. Thereafter, when power is alternately supplied to the pressure change sensing unit 20, the distance between the first pressure electrode 21a and the second pressure electrode 21b may be changed by pressure caused by the load of the passenger, and the controller 30 may be configured to determine whether the passenger is seated on the seat 1 and the type of passenger by detecting the change in the distance.

Accordingly, the controller 30 may be configured to alternately supply power to the permittivity change sensing unit 10 and the pressure change sensing unit 20, and correctly determine whether the passenger is seated on the seat 1 and the type of passenger by reading change in permittivity and change in pressurizing force alternately detected by the permittivity change sensing unit 10 and the pressure change sensing unit 20. The configurations and disposition of the permittivity change sensing unit 10 and the pressure change sensing unit 20 may be variously modified.

Figure 3:
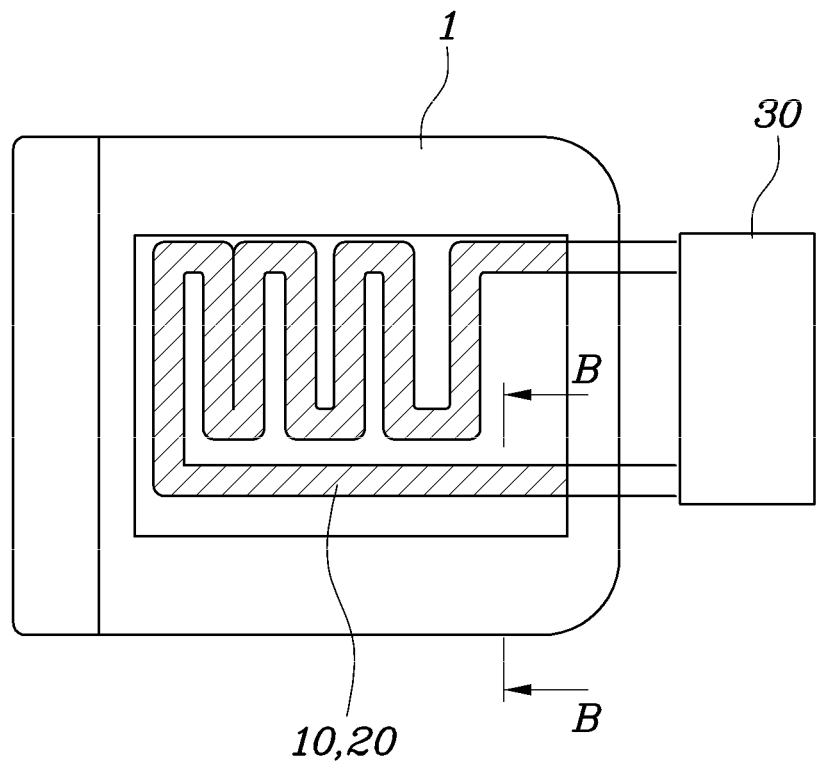
FIG. 3 is a view illustrating the configuration of a passenger identification apparatus for vehicles in accordance with a second exemplary embodiment of the present invention.
Figure 4:
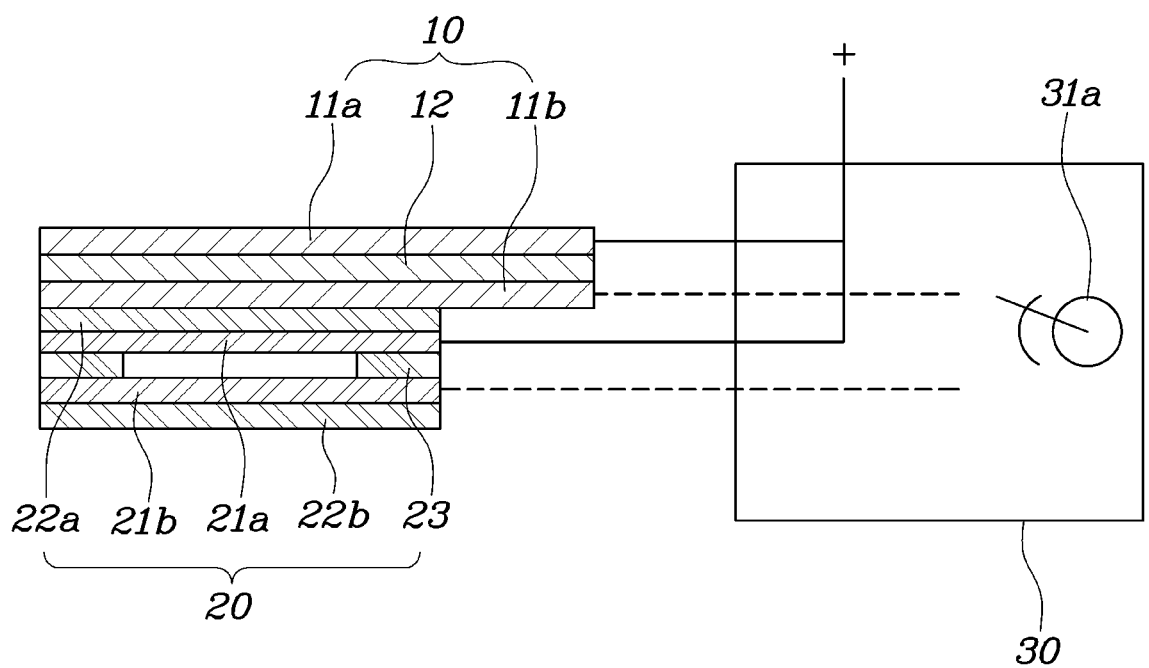
FIG. 4 is a view illustrating the configurations of a permittivity change sensing unit and a pressure change sensing unit in accordance with the second exemplary embodiment of the present invention.

FIG. 3 is a view illustrating the configuration of a passenger identification apparatus for vehicles in accordance with a second exemplary embodiment of the present invention, and FIG. 4 is a view illustrating the configurations of a permittivity change sensing unit and a pressure change sensing unit in accordance with the second exemplary embodiment of the present invention. As exemplarily shown in FIGS. 3 and 4, the passenger identification apparatus for vehicles in accordance with the second exemplary embodiment of the present invention may include a permittivity change sensing unit 10, a pressure change sensing unit 20 and a controller 30, in the same manner as the above-described first embodiment.

In particular, the functions of the permittivity change sensing unit 10, the pressure change sensing unit 20 and the controller 30 in the second exemplary embodiment are similar to those in the first exemplary embodiment. However, in the second exemplary embodiment, the disposition of the permittivity change sensing unit 10 and the pressure change sensing unit 20 is changed. For example, in the passenger identification apparatus for vehicles in accordance with the second exemplary embodiment, the permittivity change sensing unit 10 and the pressure change sensing unit 20 may be installed in the same area of a seat 1 to be disposed in the vertical direction, and may be electrically connected in parallel. Therefore, the controller 30 may include a switch 31 configured to switch between the permittivity change sensing unit 10 and the pressure change sensing unit 20 to selectively supply power to the permittivity change sensing unit 10 and the pressure change sensing unit 20.

In the same manner as the first exemplary embodiment, the permittivity change sensing unit 10 may include a first permittivity electrode 11a configured to sense change in permittivity of the passenger seated on the seat 1, a second permittivity electrode 11b spaced apart downward from the first permittivity electrode 11a to be opposite thereto and configured to prevent an ambient noise signal from being sensed by the first permittivity electrode 11a, and a first insulator 12 interposed between the first permittivity electrode 11a and the second permittivity electrode 11b to insulate the first permittivity electrode 11a and the second permittivity electrode 11b from each other.

Further, in the same manner as the first exemplary embodiment, the pressure change sensing unit 20 may include a first pressure electrode 21a and a second pressure electrode 21b which are spaced apart from each other in the vertical direction to be opposite to each other, a spacer 23 interposed between the first pressure electrode 21a and the second pressure electrode 21b to maintain a distance between the first pressure electrode 21a and the second pressure electrode 21b in response to change in the distance between the first pressure electrode 21a and the second pressure electrode 21b, and a second insulator 22a and a third insulator 22b disposed on the outer surfaces of the first pressure electrode 21a and the second pressure electrode 21b to insulate the first pressure electrode 21a and the second pressure electrode 21b.

However, the pressure change sensing unit 20 may be disposed under the permittivity change sensing unit 10, and particularly, the second insulator 22a of the pressure change sensing unit 20 may be disposed to contact the lower surface of the second permittivity electrode 11b of the permittivity change sensing unit 10. In the above-described passenger identification apparatus for vehicles in accordance with the second exemplary embodiment, if a passenger is seated on the seat 1, the controller 30 may be configured to alternately supply power to the permittivity change sensing unit 10 and the pressure change sensing unit 20.

Then, permittivity detected by the first permittivity electrode 11a is changed by the passenger, and the controller 30 may be configured to determine whether the passenger is seated on the seat 1 and a type of passenger by detecting the change in permittivity. Thereafter, when power is alternately supplied to the pressure change sensing unit 20, the load of the passenger may be transmitted to the permittivity change sensing unit 10, the pressure change sensing unit 20 may be pressurized by the load transmitted to the permittivity change sensing unit 10 and thus the distance between the first pressure electrode 21a and the second pressure electrode 21b is changed, and the controller 30 may be configured to determine whether the passenger is seated on the seat 1 and the type of passenger by detecting the change in the space.

Accordingly, the controller 30 may be configured to alternately supply power to the permittivity change sensing unit 10 and the pressure change sensing unit 20, and correctly identify whether the passenger is seated on the seat 1 and the type of passenger by reading change in permittivity and change in pressurizing force alternately detected by the permittivity change sensing unit 10 and the pressure change sensing unit 20.

Figure 5:
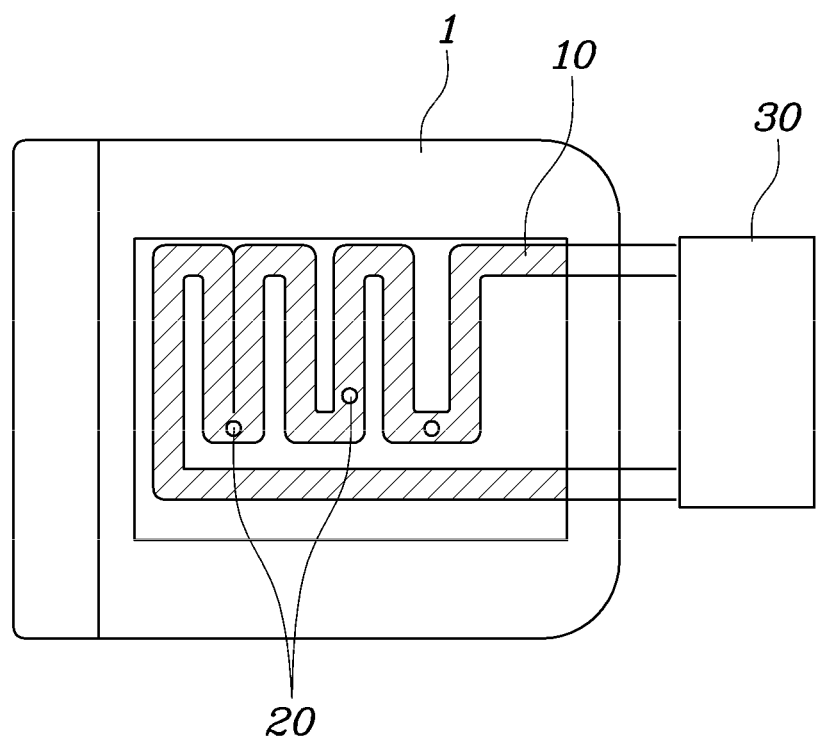
FIG. 5 is a view illustrating the configuration of a passenger identification apparatus for vehicles in accordance with a third exemplary embodiment of the present invention.

FIG. 5 is a view illustrating the configuration of a passenger identification apparatus for vehicles in accordance with a third exemplary embodiment of the present invention. As exemplarily shown in FIG. 5, the passenger identification apparatus for vehicles in accordance with the third exemplary embodiment of the present invention may include a permittivity change sensing unit 10, a pressure change sensing unit 20 and a controller 30, in the same manner as the above-described first exemplary embodiment.

However, the permittivity change sensing unit 10 and the pressure change sensing unit 20 may be installed separately in different areas of a seat 1 or may be installed in the same area of the seat 1 to be disposed in the vertical direction, and may be electrically connected in series. In particular, the controller 30 may be configured to alternately supply alternating current (AC) power provided to the permittivity change sensing unit 10 and direct current (DC) power provided to the pressure change sensing unit 20. Therefore, while AC power is supplied, the permittivity change sensing unit 10 may be configured to sense change in permittivity, and, while DC power is supplied, the pressure change sensing unit 20 may be configured to sense change in pressurizing force.

Figure 6:
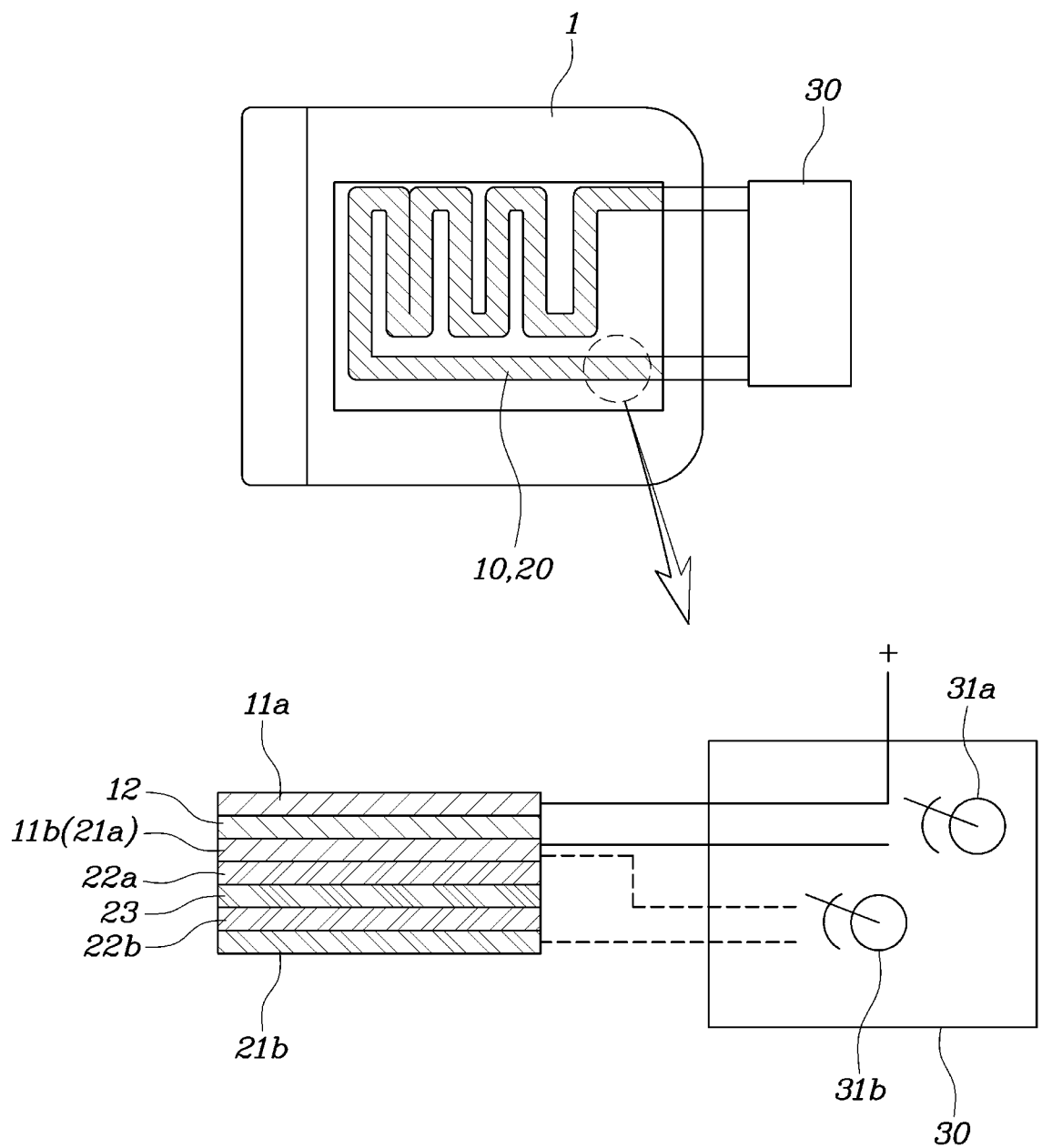
FIG. 6 is a view illustrating the configuration of a passenger identification apparatus for vehicles in accordance with a fourth exemplary embodiment of the present invention.

FIG. 6 is a view illustrating the configuration of a passenger identification apparatus for vehicles in accordance with a fourth exemplary embodiment of the present invention. As exemplarily shown in FIG. 6, the passenger identification apparatus for vehicles in accordance with the fourth exemplary embodiment of the present invention may include a permittivity change sensing unit 10, a pressure change sensing unit 20 and a controller 30, in the same manner as the above-described first exemplary embodiment.

However, in the passenger identification apparatus for vehicles in accordance with the fourth exemplary embodiment, the permittivity change sensing unit 10 and the pressure change sensing unit 20 may be installed in the same area of a seat 1 to be disposed in the vertical direction, and may be electrically connected in parallel. In particular, one electrode may be used in common as one of permittivity electrodes of the permittivity change sensing unit 10 and one of pressure electrodes of the pressure change sensing unit 20.

Therefore, the controller 30 may include one or more switches 31a and 31b to selectively supply power to the permittivity change sensing unit 10 and the pressure change sensing unit 20. When two switches 31a and 31b are provided, one of electric wires electrically connected to each of the respective switches 31a and 31b may be connected to the electrode, which is used in common in the permittivity change sensing unit 10 and the pressure change sensing unit 20 to function as both a permittivity electrode and a pressure electrode. For example, the permittivity change sensing unit 10 may include a first permittivity electrode 11a configured to sense change in permittivity of the passenger seated on the seat 1, and a first insulator 12 disposed under the first under the first permittivity electrode 11a.

Further, the pressure change sensing unit 20 may be disposed under the permittivity change sensing unit 10, and may include a first pressure electrode 21a and a second pressure electrode 21b which are spaced apart from each other in the vertical direction to be opposite to each other, a spacer 23 interposed between the first pressure electrode 21a and the second pressure electrode 21b to maintain a distance between the first pressure electrode 21a and the second pressure electrode 21b in response to change in the distance between the first pressure electrode 21a and the second pressure electrode 21b, and a second insulator 22a and a third insulator 22b interposed between the first pressure electrode 21a and the spacer 23 and between the spacer 23 and the second pressure electrode 21b to insulate the first pressure electrode 21a, the spacer 23 and the second pressure electrode 21b from one another.

The first pressure electrode 21a of the pressure change sensing unit 20 may be disposed to contact the lower surface of the first insulator 12 of the permittivity change sensing unit 10. Therefore, the first pressure electrode 21a may also serve as a second permittivity electrode 11b of the permittivity change sensing unit 10.

The controllers 30 in accordance with various exemplary embodiments of the present invention may be implemented through a processor (not shown) configured to perform an operation which will be described above, using an algorithm configured to control operations of various components of a vehicle or a non-volatile memory (not shown) configured to store data regarding software commands to reproduce the algorithm and the data stored in the corresponding memory. The memory and the processor may be implemented as separate chips. Alternatively, the memory and the processor may be implemented as one integrated chip. One or more processors may be provided.

As is apparent from the above description, a passenger identification apparatus for vehicles in accordance with the one exemplary embodiment of the present invention may identify whether a passenger is seated on a seat and a type of passenger by integrally sensing change in a load of the passenger and change in permittivity, and thus reduce a possibility of errors in passenger identification. Further, the passenger identification apparatus for vehicles may correctly identify whether a passenger is seated on a seat and a type of passenger, and thus allows an airbag to be correctly deployed as needed.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A passenger identification apparatus in a vehicle seat which identifies a passenger seated on the seat, the passenger identification apparatus comprising:

a permittivity change sensing unit installed in the seat, and configured to sense change in capacitance generated by permittivity of the passenger seated on the seat;

a pressure change sensing unit installed in the seat, and configured to sense change in pressure generated by a load of the passenger seated on the seat; and a controller configured to adjust power supplied to the permittivity change sensing unit and the pressure change sensing unit and to determine whether the passenger is seated on the seat and a type of passenger using permittivity and pressure change values sensed by the permittivity change sensing unit and the pressure change sensing unit.

2. The passenger identification apparatus according to claim 1, wherein:

the permittivity change sensing unit and the pressure change sensing unit are installed separately in different areas of the seat, and are electrically connected in parallel; and the controller includes a switch configured to switch between the permittivity change sensing unit and the pressure change sensing unit to selectively supply power to the permittivity change sensing unit and the pressure change sensing unit.

3. The passenger identification apparatus according to claim 2, wherein the permittivity change sensing unit includes:

a first permittivity electrode configured to sense change in permittivity of the passenger seated on the seat;

a second permittivity electrode spaced apart downward from the first permittivity electrode to be opposite to the first permittivity electrode, and configured to prevent an ambient noise signal from being sensed by the first permittivity electrode; and a first insulator interposed between the first permittivity electrode and the second permittivity electrode to insulate the first permittivity electrode and the second permittivity electrode from each other.

4. The passenger identification apparatus according to claim 3, wherein the pressure change sensing unit is disposed to be spaced apart from the permittivity change sensing unit in the horizontal direction, and includes:

a first pressure electrode and a second pressure electrode spaced apart from each other in the vertical direction to be opposite to each other;

a spacer interposed between the first pressure electrode and the second pressure electrode to maintain a distance between the first pressure electrode and the second pressure electrode in response to change in the distance between the first pressure electrode and the second pressure electrode; and a second insulator and a third insulator disposed on outer surfaces of the first pressure electrode and the second pressure electrode to insulate the first pressure electrode and the second pressure electrode.

5. The passenger identification apparatus according to claim 1, wherein:

the permittivity change sensing unit and the pressure change sensing unit are installed in the same area of the seat to be disposed in the vertical direction, and are electrically connected in parallel; and the controller includes a switch configured to switch between the permittivity change sensing unit and the pressure change sensing unit to selectively supply power to the permittivity change sensing unit and the pressure change sensing unit.

6. The passenger identification apparatus according to claim 5, wherein the permittivity change sensing unit includes:
- a first permittivity electrode configured to sense change in permittivity of the passenger seated on the seat;
- a second permittivity electrode spaced apart downward from the first permittivity electrode to be opposite to the first permittivity electrode, and configured to prevent an ambient noise signal from being sensed by the first permittivity electrode; and
- a first insulator interposed between the first permittivity electrode and the second permittivity electrode to insulate the first permittivity electrode and the second permittivity electrode from each other.

7. The passenger identification apparatus according to claim 6, wherein the pressure change sensing unit is disposed under the permittivity change sensing unit, and includes:
- a first pressure electrode and a second pressure electrode spaced apart from each other in the vertical direction to be opposite to each other;
- a spacer interposed between the first pressure electrode and the second pressure electrode to maintain a distance between the first pressure electrode and the second pressure electrode in response to change in the distance between the first pressure electrode and the second pressure electrode; and
- a second insulator and a third insulator disposed on outer surfaces of the first pressure electrode and the second pressure electrode to insulate the first pressure electrode and the second pressure electrode,
- wherein the second insulating of the press change sensing unit is disposed to contact a lower surface of the second permittivity electrode of the permittivity change sensing unit.

8. The passenger identification apparatus according to claim 5, wherein the permittivity change sensing unit includes:
- a first permittivity electrode configured to sense change in permittivity of the passenger seated on the seat; and
- a first insulator disposed under the first permittivity electrode.

9. The passenger identification apparatus according to claim 8, wherein the pressure change sensing unit is disposed under the permittivity change sensing unit, and includes:
- a first pressure electrode and a second pressure electrode spaced apart from each other in the vertical direction to be opposite to each other;
- a spacer interposed between the first pressure electrode and the second pressure electrode to maintain a distance between the first pressure electrode and the second pressure electrode in response to change in the distance between the first pressure electrode and the second pressure electrode; and
- a second insulator and a third insulator interposed between the first pressure electrode and the spacer and between the spacer and the second pressure electrode to insulate the first pressure electrode, the spacer and the second pressure electrode from one another,
- wherein the first pressure electrode of the pressure change sensing unit is disposed to contact a lower surface of the first insulator of the permittivity change sensing unit.

10. The passenger identification apparatus according to claim 1, wherein:
- the permittivity change sensing unit and the pressure change sensing unit are installed separately in different areas of the seat or are installed in the same area of the seat to be disposed in the vertical direction, and are electrically connected in series; and
- the controller is configured to alternately supply alternating current power provided to the permittivity change sensing unit and direct current power provided to the pressure change sensing unit.

* * * * *